United States Patent [19]
Fisher

[11] Patent Number: 6,071,696
[45] Date of Patent: Jun. 6, 2000

[54] METHOD OF PRODUCING A TEMPORALLY SPACED SUBTRACTED (TSS) CDNA LIBRARY AND USE THEREOF TO MONITOR DIFFERENTIATION

[75] Inventor: Paul B. Fisher, Scarsdale, N.Y.

[73] Assignee: The Trustees of Columbia University in the City of New York, New York, N.Y.

[21] Appl. No.: 08/774,465

[22] Filed: Dec. 30, 1996

[51] Int. Cl.[7] .......................... C12Q 1/68; G01N 33/574; G01N 33/48
[52] U.S. Cl. ................................ 435/6; 435/7.23; 436/63; 436/64
[58] Field of Search ..................... 435/7.2, 7.23; 436/63, 64; 530/300

[56] References Cited

FOREIGN PATENT DOCUMENTS

WO 95/11986  5/1995  European Pat. Off. .

OTHER PUBLICATIONS

Jiang et al, "A molecular definition of terminal cell differentiation in human melanoma cells" Mol. and Cell. Diff. vol. 2 (3), pp. 221–239, 1994.

Fisher et al, "Effect of recombinant human fibroblast interferon and mezerein on growth differentiation immune interferaon binding and tumor associated antigen expression in human melanoma cells" Anticancer Res. vol. 6(4), pp. 765–774, 1986.

Hara, E., et al. (1993) *Anal. Biochem.*, 214:58–64 (Exhibit B).

Rubenstein, J.L.R., et al. (1990) *Nucleic Acids Research*, 18(16): 4833–42 (Exhibit C).

Hara, E., et al. (1991) *Nucleic Acids, Research*, 19(25) 7097–7104 (Exhibit D).

Maniatis, T., et al. (1982) *Molecular Cloning: A Laboratory Manual*, Cold Spring Harbor Laboratory, pp. 224–228 (Exhibit E).

Travis, G., et al. (1988) *Proc. Natl. Acad. Sci., USA*, 85:1696–1700 (Exhibit F).

Duguid, J.R., et al. (1988) *Proc. Natl. Acad. Sci., USA*, 85:5738–5742 (Exhibit G).

Herfort, M.R., and Garber, A.T. (1991) *BioTechniques*, 11(5):598–603 (Exhibit H).

Lee, S.W., et al. (1991) *Proc. Natl. Acad. Sci., USA*, 88:2825–2829 (Exhibit I).

Sive, H.L., et al. (1988) *Nucleic Acids Research*, 16(22):10937 (Exhibit J).

Wieland, I., et al. (1990) *Proc. Natl. Acad. Sci., USA*, 87:2720–2724 (Exhibit K).

*Primary Examiner*—Yvonne Eyler
*Attorney, Agent, or Firm*—John P. White; Cooper & Dunham LLP

[57] ABSTRACT

This invention provides a method for producing a temporally spaced subtracted cDNA library comprising: a) isolating temporally spaced RNAs from cells; b) generating cDNA inserts from the RNAs isolated from step (a); c) producing a temporally spaced cDNA library having clones containing the cDNA inserts generated from step (b); d) producing double stranded cDNA inserts from the temporally spaced cDNA library; e) denaturing the double stranded cDNA inserts; f) contacting the denatured double stranded cDNA inserts produced in step (e) with single-stranded DNAs from another cDNA library under conditions permitting hybridization of the single-stranded DNAs and the double-stranded cDNA inserts; g) separating the hybridized cDNA inserts from the unhybridized inserts; h) generating a cDNA library of the unhybridized inserts, thereby generating a temporally spaced subtracted cDNA library. The cDNAs are then used to monitor cellular differention.

3 Claims, 7 Drawing Sheets

FIGURE 6C

Human RNA Master Blot Code

|   | 1 | 2 | 3 | 4 | 5 | 6 | 7 | 8 |
|---|---|---|---|---|---|---|---|---|
| A | whole brain | amygdala | caudate nucleus | cerebellum | cerebral cortex | frontal lobe | hippocampus | medulla oblongada |
| B | occipital lobe | putamen | substantia nigra | temporal lobe | thalamus | sub-thalamic nucleus | spinal cord | |
| C | heart | aorta | skeletal muscle | colon | bladder | uterus | prostate | stomach |
| D | testis | ovary | pancreas | pituitary gland | adrenal gland | thyroid gland | salivary gland | mammary gland |
| E | kidney | liver | small intestine | spleen | thymus | peripheral leukocyte | lymph node | bone marrow |
| F | appendix | lung | trachea | placenta | | | | |
| G | fetal brain | fetal heart | fetal kidney | fetal liver | fetal spleen | fetal thymus | fetal lung | |
| H | yeast total RNA 100ng | yeast tRNA 100ng | E coli tRNA 100ng | E coli DNA 100ng | poly r(A) 100ng | human $C_0t$ 1 DNA 100ng | human DNA 100ng | human DNA 500ng |

METHOD OF PRODUCING A TEMPORALLY SPACED SUBTRACTED (TSS) CDNA LIBRARY AND USE THEREOF TO MONITOR DIFFERENTIATION

STATEMENT REGARDING FEDERALLY FUNDED RESEARCH

The invention disclosed herein was made with Government support under National Cancer Institute Grant No. CA35675. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Terminal differentiation in human melanoma cells correlates with temporal changes in the expression of specific target genes. To define those genes that may be critical for this process a subtraction hybridization approach was used. cDNA libraries were constructed from actively proliferating H0-1 human melanoma cells (driver cDNA library) and cultures treated for various time periods with the combination of recombinant human fibroblast interferon (IFN-β) and mezerein (MEZ) (temporally spaced tester cDNA library) that induces terminal differentiation (Jiang and Fisher, 1993). From these two cDNA libraries, an H0-1 IFN-β+ MEZ temporally spaced subtracted (TSS) cDNA library was constructed. Random screening of this TSS cDNA library identifies cDNAs that display differential expression as a function of induction of growth arrest and terminal differentiation, called melanoma differentiation associated (mda) genes. In the present study the properties of the novel mda-9 gene were analyzed. This cDNA encodes a unique protein of 298 amino acids with a predicted size of ~34 kDa. Southern blotting analysis indicates that mda-9 is an evolutionary conserved gene. Tissue distribution analysis documents comparable expression in fifty human tissues, with slightly elevated expression in brain (putamen) and spleen (adult and fetal). Treatment of H0-1 human melanoma cells with IFN-β+MEZ results in a biphasic induction of mda-9 with maximum expression 8 and 12 h post-treatment and reduced expression at 24 h. In terminally differentiated and irreversibly growth arrested human melanoma cells, the level of mda-9 mRNA is reduced. The suppression in mda-9 expression is not simply a function of growth inhibition, since treatment of H0-1 cells with interferons, including IFN-β, leukocyte interferon (IFN-α) or immune interferon (IFN-γ), elevates mda-9 expression even though they suppress growth. These studies demonstrate that subtraction hybridization using temporally spaced RNA samples, resulting in a TSS cDNA library, can identify genes, such as mda-9, that are down-regulated during terminal cell differentiation in human melanoma cells. Further studies are necessary to define the precise role of mda-9 in the process of terminal differentiation.

Cancer is a progressive disease characterized by both qualitative and quantitative changes in the phenotypes of evolving tumor cells (1–5). Although cancer can develop as a consequence of single or multiple genetic alterations, a common theme in carcinogenesis involves abnormal programs of differentiation (6–10). Attempts to exploit this defective differentiation process in cancer cells has led to the development of a therapeutic approach called 'differentiation therapy' (6–11). This strategy is based on the use of single or multiple agents that induce cancer cells to become more differentiated with a concomitant reduction or loss of growth potential (6–12). In order to utilize differentiation therapy as an effective clinical tool, further research is necessary to identify agents capable of efficiently inducing terminal differentiation in cancer cells without inducing nonspecific toxicity in normal cells. Additionally, the identification of genes that correlate with and may mediate terminal cell differentiation would represent valuable reagents for defining the molecular basis of terminal cell differentiation, for direct cancer therapeutic applications and for screening compounds for potential use in differentiation therapy (6–12). In cultured human melanoma cells, the combination of IFN-β+MEZ results in terminal cell differentiation and an irreversible loss of proliferative potential (11,13,14). In this model system, a single treatment for 24 h is sufficient to induce >95% terminal differentiation in cells subsequently grown for 72 h in the absence of inducers (14,15). The rapid induction of terminal differentiation in the vast majority of treated cancer cells makes this system amenable for defining those gene expression changes that occur during and that may mediate this process (11,12, 16–19). To begin to address on a molecular level the question of growth control and terminal differentiation in human melanoma cells and to directly clone genes involved in these processes we developed and used an efficient subtraction hybridization protocol (16). This approach has resulted in the cloning of both known and novel cDNAs that are differentially regulated during growth suppression, reversible differentiation and terminal differentiation in human melanoma and other cancer cell types (16–20). In the present study, the properties of a novel mda-9 gene identified by subtraction hybridization were described. mda-9 is an evolutionary conserved gene that encodes a protein of ~34 kDa without sequence homology to previously identified proteins. Expression of mda-9 is seen in fifty human tissues, with slightly elevated expression in brain (putamen) and spleen (adult and fetal). Induction of growth suppression and differentiation in human melanoma cells following exposure to IFN-β+MEZ results in a decrease in mda-9 expression. These studies provide additional support for the hypothesis that induction of terminal differentiation and irreversible growth arrest in human melanoma cells involves multiple gene expression changes, including increases as well as decreases in the expression of specific target genes.

SUMMARY OF THE INVENTION

This invention provides a method for producing a temporally spaced subtracted cDNA library comprising: a) isolating temporally spaced RNAs from cells; b) generating cDNA inserts from the RNAs isolated from step (a); c) producing a temporally spaced cDNA library having clones containing the cDNA inserts generated from step (b); d) producing double stranded cDNA inserts from the temporally spaced cDNA library; e) denaturing the double stranded cDNA inserts; f) contacting the denatured double stranded cDNA inserts produced in step (e) with single-stranded DNAs from another cDNA library under conditions permitting hybridization of the single-stranded DNAs and the double-stranded cDNA inserts; g) separating the hybridized cDNA inserts from the unhybridized inserts; h) generating a cDNA library of the unhybridized inserts, thereby generating a temporally spaced subtracted cDNA library.

This invention further provides a temporally spaced subtracted library generated by the method for producing a temporally spaced subtracted cDNA library comprising: a) isolating temporally spaced RNAs from cells; b) generating cDNA inserts from the RNAs isolated from step (a) ; c) producing a temporally spaced cDNA library having clones containing the cDNA inserts generated from step (b); d) producing double stranded cDNA inserts from the temporally spaced cDNA library; e) denaturing the double stranded cDNA inserts; f) contacting the denatured double stranded cDNA inserts produced in step (e) with single-stranded DNAs from another cDNA library under conditions permitting hybridization of the single-stranded DNAs and the double-stranded cDNA inserts; g) separating the hybridized cDNA inserts from the unhybridized inserts; h) generating a cDNA library of the unhybridized inserts, thereby generating a temporally spaced subtracted cDNA library.

This invention provides a temporally spaced subtracted library generated by using H0-1 melanoma cells treated with IFN-β and MEZ in a temporally spaced manner at 2, 4, 8, 12, 24, and 48 hours and, wherein the single-stranded nucleic acid molecules are from another cDNA library of H0-1 melanoma cells.

This invention provides a method of identifying a melanoma differentiation associated gene comprising: a) generating probes from clones of the temporally spaced subtracted library generated by using H0-1 melanoma cells treated with IFN-β and MEZ in a temporally spaced manner at 2, 4, 8, 12, 24, and 48 hours and cells, wherein the single-stranded nucleic acid molecules are from another cDNA library of H0-1 melanoma cells; and b) hybridizing the probe with the total RNAs or mRNAs from H0-1 cells treated with IFN-S and MEZ and the total RNAs or mRNAs from untreated H0-1 cells, hybridization of the probe with the total RNAs or mRNAs from the treated H0-1 cell but altered [no, reduced, or enhanced] hybridization with the total RNAs or mRNA from untreated cells indicating that the clone from which the probe is generated carries a melanoma differentiation associated gene.

This invention provides a melanoma differentiation associated gene identified by the above described method of identifying a melanoma differentiation associated gene.

This invention provides a method of identifying temporally expressed genes from a single subtracted cDNA library, comprising: a) cloning the cDNAs from the temporally spaced subtracted cDNA library produced by the above described method for producing a temporally spaced subtracted cDNA library ; b) hybridizing the clones obtained in step (a) with total RNAs isolated from control and with RNAs from differentiation-inducer treated cells, hybridization of the probe RNAs from differentiation-inducer treated cells, either enhanced or no or reduced hybridization with total RNA isolated from control cells indicating that the gene from which the probe was isolated is temporally expressed, thereby identifying temporally expressed genes from a single subtracted cDNA library.

This invention provides a temporally expressed gene identified by the above described method.

This invention provides an isolated mda-9 gene.

This invention provides a method for identifying a compound capable of inducing terminal differentiation in cancer cells comprising: a) incubating an appropriate concentration of the cancer cells with an appropriate concentration of the compound; b) measuring the expression of mda-9, the reduced expression of mda-9 gene indicating that the compound is capable of inducing terminal differentiation in cancer cells.

This invention provides a method for identifying a compound capable of inducing specific patterns of DNA damage caused by UV irradiation and gamma irradiation in human melanoma cells comprising: a) incubating an appropriate concentration of the human melanoma cells with an appropriate concentration of the compound; and b) measuring the expression of mda-9, the altered expression of mda-9 gene indicating that the compound is capable of inducing specific patterns of DNA damage caused by UV irradiation and gamma irradiation in human melanoma cells.

This invention provides a method for identifying a temporally expressed gene from cancer cells induced to undergo apoptosis by a chemotherapeutic agent, comprising: a) incubating an appropriate concentration of the cancer cells with an appropriate concentration of the chemotherapeutic agent; and b) measuring the expression of mda-9, the modified expression of mda-9 gene indicating that the compound is capable of inducing the cancer cells to undergo apoptosis.

This invention provides a method for identifying a compound capable of elevating mda-9 expression in cancer cells comprising: a) incubating an appropriate concentration of the cancer cells with an appropriate concentration of the compound; b) measuring the expression of mda-9 to determine whether the expression of the mda-9 gene is elevated.

This invention provides a method for detecting the presence of cytokines in a sample comprising a) contacting the sample with cancerous cells; b) measuring the expression of the mda-9 gene; c) determining whether the expression of the mda-9 gene is altered, the altered expression of the mda-9 gene in the cancerous cells indicating the presence of cytokines.

This invention provides an antisense oligonucleotide having a sequence capable of specifically hybridizing to an mRNA molecule encoding a human mda-9 protein so as to prevent expression of the mRNA molecule. This invention provides an antisense oligonucleotide having a sequence capable of specifically hybridizing to an mRNA molecule encoding a human mda-9 protein so as to prevent translation of the mRNA molecule.

This invention provides an antisense oligonucleotide having a sequence capable of specifically hybridizing to the promoter of the isolated nucleic acid molecule of an mda-9 gene, wherein the encoded mda-9 protein is a human protein, thereby preventing mRNA transcription.

This invention provides an antisense oligonucleotide having a sequence capable of specifically hybridizing to the mRNA of the isolated nucleic acid molecule of an mda-9 gene, wherein the encoded mda-9 protein is a human protein, and capable of degrading the hybridized mRNA.

This invention provides a purified mda-9 protein. This invention provides a purified human mda-9 protein. This invention provides an antibody directed to a purified mda-9 protein. This invention further provides an antibody capable of specifically recognizing an mda-9 protein. In an embodiment of the invention, the antibody is capable of specifically recognizing a human mda-9 protein.

This invention provides a pharmaceutical composition comprising an amount of the antisense oligonucleotide having a sequence capable of specifically hybridizing to an mRNA molecule encoding a human mda-9 protein so as to prevent expression of the mRNA molecule, to prevent translation of the mRNA molecule, effective to prevent expression of a human mda-9 protein and a pharmaceutically acceptable carrier. This invention also provides a pharmaceutical composition comprising an amount of the antisense oligonucleotide having a sequence capable of specifically hybridizing to the promoter of the isolated nucleic acid molecule of an mda-9 gene, wherein the encoded mda-9 protein is a human protein, thereby preventing mRNA transcription, effective to prevent expression of a human mda-9 protein and a pharmaceutically acceptable carrier. This invention further provides a pharmaceutical composition comprising an amount of the antisense oligonucleotide having a sequence capable of specifically hybridizing to the mRNA of the isolated nucleic acid molecule of an mda-9 gene, wherein the encoded mda-9 protein is a human protein and capable of degrading the hybridized mRNA, effective to prevent expression of a human mda-9 protein and a pharmaceutically acceptable carrier.

This invention provides a method of treating melanoma in a subject by administering a pharmaceutical composition comprising an amount of any one of the above described antisense oligonucleotides effective to prevent expression of a human mda-9 protein and a pharmaceutically acceptable carrier, thereby treating melanoma in a subject.

This invention provides a method of administering a pharmaceutical composition comprising an amount of any one of the above described antisense oligonucleotides effective to prevent expression of a human mda-9 protein and a pharmaceutically acceptable carrier.

This invention provides a method of inhibiting expression of a mda-9 gene in a subject comprising introducing a vector containing a nucleic acid molecule which renders the mda-9 gene functionless into the subject under conditions permitting the inhibition of the expression of the mda-9 gene.

This invention provides a method of treating a cancer in a subject by administering a pharmaceutical composition comprising an effective amount of the antibody capable of specifically recognizing an mda-9 protein, thereby treating the cancer in a subject.

DETAILED DESCRIPTION OF THE INVENTION

Figure 1:
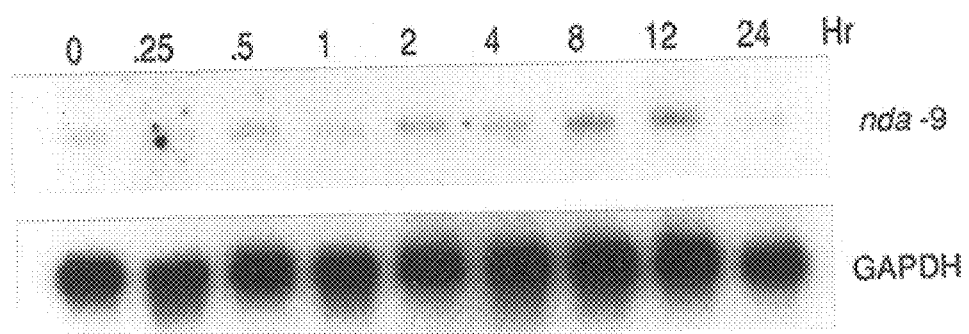
FIG. 1. Temporal expression of mda-9 in H0-1 cells exposed to IFN-β+MEZ. RNAs were isolated from untreated and H0-1 cells treated with IFN-9 +MEZ(2000 U/ml+10 ng/ml) for 0.25, 0.5, 1, 2, 4, 8, 12 and 24 h. Ten micrograms of total cellular RNA were separated on 1 agarose gel, transferred to nylon membranes, sequentially hybridized with an mda-9 and then a GAPDH probe, and then exposed to autoradiography.

This invention provides a method for producing a temporally spaced subtracted cDNA library comprising: a) isolating temporally spaced RNAs from cells; b) generating cDNA inserts from the RNAs isolated from step (a); c) producing a temporally spaced cDNA library having clones containing the cDNA inserts generated from step (b); d) producing double stranded cDNA inserts from the temporally spaced cDNA library; e) denaturing the double stranded cDNA inserts; f) contacting the denatured double stranded cDNA inserts produced in step (e) with single-stranded DNAs from another cDNA library under conditions permitting hybridization of the single-stranded DNAs and the double-stranded cDNA inserts; g) separating the hybridized cDNA inserts from the unhybridized inserts; h) generating a cDNA library of the unhybridized inserts, thereby generating a temporally spaced subtracted cDNA library.

As used herein "temporally spaced RNAs" are defined as RNAs collected over a sequential period of time. As used herein "temporally spaced subtracted cDNA library" is a cDNA library generated using a temporally spaced cDNA library having clones containing the cDNA inserts generated from temporally spaced RNAs to which single-stranded DNAs from another cDNA library are hybridized and separated, resulting in the "subtracted" unhybridized cDNA insert library.

In an embodiment of the invention, the cDNA library used to generate the single-stranded DNAs is from the same cell population as the cell population used to generate the temporally spaced cDNA library. In a further embodiment of the invention, the cDNA library allows propagation in single-stranded circle form. In a preferred embodiment of the invention, the cDNA library is a λZAP cDNA library.

In an embodiment of the invention, the double stranded cDNA inserts in step (d) are produced by releasing double-stranded cDNA inserts from double-stranded cDNA clones of the temporally spaced cDNA library with appropriate restriction enzymes. In another embodiment of the invention, the single-stranded cDNAs are labeled with biotin. In an embodiment of the invention, the separating of step f) is performed by extraction with streptavidin-phenol:chloroform. In a preferred embodiment of the invention, the cells are H0-1 human melanoma cells treated with IFN-9 and MEZ. In a preferred embodiment of the invention, the treatment with IFN-β and MEZ is temporally spaced. In a further preferred embodiment of the invention, the temporally spaced treatment occurs at 2, 4, 8, 12, 24, and 48 hours.

In an embodiment of the invention, the single-stranded nucleic acid molecules are from another cDNA library of H0-1 melanoma cells. In a further embodiment of the invention, the cells are terminally differentiated and the single-stranded cDNAs are from another cDNA library of undifferentiated cells. In another embodiment of the invention, the cells are undifferentiated and the single-stranded cDNAs are from another cDNA library of terminally differentiated cells.

In a preferred embodiment of the invention, the cells are cancerous cells. In a further embodiment of the invention, the cancerous cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells and lymphoma cells.

In an embodiment of the invention, the cells are induced to undergo reversible growth arrest, DNA damage, or apoptosis and the single-stranded cDNAs are from another cDNA library of uninduced cells. In another embodiment of the invention, the cells are uninduced cells and the single-stranded cDNAs are from cells induced to undergo reversible growth arrest, DNA damage, or apoptosis.

As used herein, apoptosis is defined as programmed cell death.

In an embodiment of the invention, the cells are at one developmental stage and the single-stranded cDNAs are from another cDNA library of the cells at a different developmental stage. In another embodiment of the invention, the cells are cancerous and the single-stranded cDNAs are from another cDNA library from normal cells. In an embodiment of the invention, the cells are from the skin, connective tissue, muscle, breast, brain, meninges, spinal cord, colon, endometrium, lung, prostate and ovary.

This invention further provides a method further comprising introducing the subtracted library into host cells. In an embodiment of the invention, the method further comprises ligating the subtracted inserts into λ Uni-ZAP arms.

This invention further provides a temporally spaced subtracted library generated by the method for producing a temporally spaced subtracted cDNA library comprising: a) isolating temporally spaced RNAs from cells; b) generating cDNA inserts from the RNAs isolated from step (a); c) producing a temporally spaced cDNA library having clones containing the cDNA inserts generated from step (b); d) producing double stranded cDNA inserts from the temporally spaced cDNA library; e) denaturing the double stranded cDNA inserts; f) contacting the denatured double stranded cDNA inserts produced in step (e) with single-stranded DNAs from another cDNA library under conditions permitting hybridization of the single-stranded DNAs and the double-stranded cDNA inserts; g) separating the hybridized cDNA inserts from the unhybridized inserts; h) generating a cDNA library of the unhybridized inserts, thereby generating a temporally spaced subtracted cDNA library.

This invention provides a temporally spaced subtracted library generated by using H0-1 melanoma cells treated with IFN-β and MEZ in a temporally spaced manner at 2, 4, 8, 12, 24, and 48 hours and, wherein the single-stranded nucleic acid molecules are from another cDNA library of H0-1 melanoma cells.

This invention provides a method of identifying a melanoma differentiation associated gene comprising: a) generating probes from clones of the temporally spaced subtracted library generated by using H0-1 melanoma cells treated with IFN-β and MEZ in a temporally spaced manner at 2, 4, 8, 12, 24, and 48 hours and cells, wherein the single-stranded nucleic acid molecules are from another cDNA library of H0-1 melanoma cells; and b) hybridizing the probe with the total RNAs or mRNAs from H0-1 cells treated with IFN-β and MEZ and the total RNAs or mRNAs from untreated H0-1 cells, hybridization of the probe with the total RNAs or mRNAs from the treated H0-1 cell but altered [no, reduced, or enhanced] hybridization with the total RNAs or mRNA from untreated cells indicating that the clone from which the probe is generated carries a melanoma differentiation associated gene. In an embodiment of the invention, the mRNAs are probed with labeled cDNA clones generated from the temporally spaced subtracted library on a dot blot, hybridization of the probe with the mRNAs isolating a melanoma differentiation associated gene.

This invention provides a melanoma differentiation associated gene identified by the above described method of of identifying a melanoma differentiation associated gene.

This invention provides a method of identifying temporally expressed genes from a single subtracted cDNA library, comprising: a) cloning the cDNAs from the temporally spaced subtracted cDNA library produced by the above desribed method for producing a temporally spaced subtracted cDNA library; b) hybridizing the clones obtained in step (a) with total RNAs isolated from control and with RNAs from differentiation-inducer treated cells, hybridization of the probe RNAs from differentiation-inducer treated cells, either enhanced or no or reduced hybridization with total RNA isolated from control cells indicating that the gene from which the probe was isolated is temporally expressed, thereby identifying temporally expressed genes from a single subtracted cDNA library.

This invention provides a temporally expressed gene identified by the above described method. In an embodiment of the invention, the temporally expressed gene is cloned into a λ ZAP phage vector.

This invention provides an isolated mda-9 gene. In an embodiment of the invention, the isolated mda-9 gene is an isolated nucleic acid, wherein the encoded mda-9 protein is a human protein.

This invention provides a method for identifying a compound capable of inducing terminal differentiation in cancer cells comprising: a) incubating an appropriate concentration of the cancer cells with an appropriate concentration of the compound; b) measuring the expression of mda-9, the reduced expression of mda-9 gene indicating that the compound is capable of inducing terminal differentiation in cancer cells. In an embodiment of the invention, the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells and lymphoma cells.

This invention provides a method for identifying a compound capable of inducing specific patterns of DNA damage caused by UV irradiation and gamma irradiation in human melanoma cells comprising: a) incubating an appropriate concentration of the human melanoma cells with an appropriate concentration of the compound; and b) measuring the expression of mda-9, the altered expression of mda-9 gene indicating that the compound is capable of inducing specific patterns of DNA damage caused by UV irradiation and gamma irradiation in human melanoma cells.

This invention provides a method for identifying a temporally expressed gene from cancer cells induced to undergo apoptosis by a chemotherapeutic agent, comprising: a) incubating an appropriate concentration of the cancer cells with an appropriate concentration of the chemotherapeutic agent; and b) measuring the expression of mda-9, the modified expression of mda-9 gene indicating that the compound is capable of inducing the cancer cells to undergo apoptosis. In an embodiment of the invention, the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells and lymphoma cells.

This invention provides a method for identifying a compound capable of elevating mda-9 expression in cancer cells comprising: a) incubating an appropriate concentration of the cancer cells with an appropriate concentration of the compound; b) measuring the expression of mda-9 to determine whether the expression of the mda-9 gene is elevated. In an embodiment of the invention, the compound capable of elevating mda-9 expression in cancer cells is IFN-γ. In another embodiment of the invention, the compound capable of elevating mda-9 expression in cancer cells is a cytokine. In a further embodiment of the invention, the cytokine is selected from a group consisting of IFN-α, IFN-β, IFN-γ, TNF-α, stem cell growth factors, colony stimulating factor, GMCSF, and interleukins [including interleukin-6]. In a still further embodiment of the invention, the cancer cells are selected from a group consisting of human melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells and lymphoma cells.

This invention provides a method for detecting the presence of cytokines in a sample comprising a) contacting the sample with cancerous cells; b) measuring the expression of the mda-9 gene; c) determining whether the expression of the mda-9 gene is altered, the altered expression of the mda-9 gene in the cancerous cells indicating the presence of cytokines.

This invention provides an antisense oligonucleotide having a sequence capable of specifically hybridizing to an mRNA molecule encoding a human mda-9 protein so as to prevent expression of the mRNA molecule. This invention provides an antisense oligonucleotide having a sequence capable of specifically hybridizing to an mRNA molecule encoding a human mda-9 protein so as to prevent translation of the mRNA molecule.

This invention provides an antisense oligonucleotide having a sequence capable of specifically hybridizing to the promoter of the isolated nucleic acid molecule of an mda-9 gene, wherein the encoded mda-9 protein is a human protein, thereby preventing mRNA transcription.

This invention provides an antisense oligonucleotide having a sequence capable of specifically hybridizing to the mRNA of the isolated nucleic acid molecule of an mda-9 gene, wherein the encoded mda-9 protein is a human protein, and capable of degrading the hybridized mRNA.

This invention provides a purified mda-9 protein. This invention provides a purified human mda-9 protein.

This invention provides an antibody directed to a purified mda-9 protein. This invention further provides an antibody capable of specifically recognizing an mda-9 protein. In an embodiment of the invention, the antibody is capable of specifically recognizing a human mda-9 protein. In an embodiment of the invention, the antibody is a monoclonal or polyclonal antibody directed to a purified mda-9 protein. In another embodiment of the invention, the antibody is a monoclonal or polyclonal antibody capable of specifically recognizing an mda-9 protein. In another embodiment of the invention, the antibody is a monoclonal or polyclonal antibody capable of specifically recognizing a human mda-9 protein. The above-described antibody is also useful for the detection of mda-9 protein.

This invention provides a pharmaceutical composition comprising an amount of the antisense oligonucleotide having a sequence capable of specifically hybridizing to an mRNA molecule encoding a human mda-9 protein so as to prevent expression of the mRNA molecule, to prevent translation of the mRNA molecule, effective to prevent expression of a human mda-9 protein and a pharmaceutically acceptable carrier. This invention also provides a pharmaceutical composition comprising an amount of the antisense oligonucleotide having a sequence capable of specifically hybridizing to the promoter of the isolated nucleic acid molecule of an mda-9 gene, wherein the encoded mda-9 protein is a human protein, thereby preventing mRNA transcription, effective to prevent expression of a human mda-9 protein and a pharmaceutically acceptable carrier. This invention further provides a pharmaceutical composition comprising an amount of the antisense oligonucleotide having a sequence capable of specifically hybridizing to the mRNA of the isolated nucleic acid molecule of an mda-9 gene, wherein the encoded mda-9 protein is a human protein and capable of degrading the hybridized mRNA, effective to prevent expression of a human mda-9 protein and a pharmaceutically acceptable carrier.

This invention provides a method of treating cancer in a subject by administering the above described pharmaceutical composition comprising an amount of any one of the above described antisense oligonucleotides effective to prevent expression of a human mda-9 protein and a pharmaceutically acceptable carrier, thereby treating melanoma in a subject. In an embodiment, the cancer is is selected from a group consisting of human melanoma, basal cell carcinoma, squamous cell carcinoma, neuroblastoma, glioblastoma multiforme carcinoma, myeloid leukemia, breast carcinoma, colon carcinoma, endometrial carcinoma, lung carcinoma, ovarian carcinoma, prostate carcinoma, cervical carcinoma, osteosarcoma and lymphoma.

In an embodiment of the subject invention, the expression of a human mda-9 gene or protein is prevented by hybridization of an antisense oligonucleotide which is operatively linked to a tissue specific promoter which is capable of directing the expression of the antisense oligonucleotide in the specific cancer cells. As used herein, "operatively linked" shall mean that the expression of the antisense oligonucleotide is controlled by the tissue specific promoter. In another embodiment, the expression of a human mda-9 protein is prevented by hybridization of the antisense oligonucleotide to the mda-9 gene promoter or mda-9 mRNA molecules regulated by a tissue specific promoter that permits expression of the human mda-9 antisense sequence only in melanocyte and melanoma cells. In a further embodiment, the cancer is melanoma and the tissue specific promoter is a tyrosinase promoter.

This invention provides a method of administering a pharmaceutical composition comprising an amount of any one of the above described antisense oligonucleotides effective to prevent expression of a human mda-9 protein and a pharmaceutically acceptable carrier. In an embodiment of the invention, pharmaceutical composition further comprises a substance which facilitates the delivery of said oligonucleotide into the cell. As used herein, the substance which facilitates the delivery of the oligonucleotide into the cell may be a liposome or an antibody. In an embodiment of the invention, the oligonucleotide is introduced into the cell by a viral vector. In an embodiment of the invention, the oligonucleotide is stabilized, so as not to be degraded.

This invention provides a method of inhibiting expression of a mda-9 gene in a subject comprising introducing a vector containing a nucleic acid molecule which renders the mda-9 gene functionless into the subject under conditions permitting the inhibition of the expression of the mda-9 gene.

As used herein, "functionless" is defined as inability of the mda-9 gene to encode the mda-9 protein, including inability to transcribe the mda-9 gene, or inability to translate the mda-9 protein.

In an embodiment of the invention, the nucleic acid is an antisense oligonucleotide having a sequence capable of specifically hybridizing to an mRNA molecule encoding a human mda-9 protein. In another embodiment of the invention, the nucleic acid contains a mutation or deletion of the mda-9 gene having the appropriate flanking sequences.

As used herein, the appropriate flanking sequences are defined as the sequences required in order for recombination to occur.

This invention provides a method of treating a cancer in a subject by administering a pharmaceutical composition comprising an effective amount of the antibody capable of specifically recognizing an mda-9 protein, thereby treating the cancer in a subject. In an embodiment of the invention, the cancer is a melanoma.

This invention will be better understood from the Experimental Details which follow. However, one skilled in the art will readily appreciate that the specific methods and results discussed are merely illustrative of the invention as described more fully in the claims which follow thereafter.
Experimental Details Cell Lines and Culture Conditions. H0-1 is a melanotic melanoma cell line produced from a metastatic inguinal lymph node lesion from a 49 year-old female and was used between passages 150 and 175 (13,21,22). FM516-SV is a normal human melanocyte culture immortalized by the SV40 T-antigen gene (23). Additional melanoma cell lines established from patients with metastatic melanomas that were evaluated, include L0-1, SH-1, WM239, MeWo, SKMEL-p53 wt (containing a wild-type p53 gene) and SKMEL-p53 mut (containing a mutant p53 gene) (13,21, 24). Cultures were grown at 37° C. in a 95% air 5% $CO_2$-humidified incubator in Dulbecco's modified Eagle's medium (DMEM) supplemented with 5 or 106 fetal bovine serum (Hyclone, Utah). Cultures were maintained in the logarithmic phase of growth by subculturing (1:5 or 1:10) prior to confluence approximately every 4 to 7 d. For determining steady-state RNA expression, cultures were seeded at $1.5\times10^6$ cells per 10-cm tissue culture plate, and 24 h later the medium was changed without inducers or with IFN-β (2000 U/ml), MEZ (10 ng/ml) or IFN-β+MEZ (2000 U/ml+10 ng/ml). Total cytoplasmic RNA was isolated at various time points and analyzed for mda-9 and GAPDH expression.

Cloning of mda-9 by Subtraction Hybridization. Identification and cloning of mda-9 was accomplished as described previously (16). Briefly, a cDNA library was prepared from RNA isolated from actively growing H0-1 cells (driver) and RNAs isolated from H0-1 cells treated with IFN-β+MEZ (2000 U/ml+10 ng/ml) for 2, 4, 8, 12 and 24 h (temporally spaced tester). Subtraction hybridization was then performed between double-stranded tester DNA and single-stranded driver DNA prepared by mass excision of the libraries. The TSS cDNAs were efficiently cloned into the λ Uni-ZAP phage vector and used to screen Northern blots containing total RNA isolated from control H0-1 cells and H0-1 cultures treated for 24 h with IFN-β (2000 U/ml), MEZ (10 ng/ml) or IFN-β+MEZ (2000 U/ml+10 ng/ml). This strategy resulted in the identification of a partial mda-9 cDNA (11). A full-length mda-9 cDNA was isolated following screening of a differentiation inducer-treated H0-1 cDNA library (16) and using the procedure of rapid amplification of cDNA ends (RACE) as described previously (17,25–27). Sequence analysis was determined as described (28,29).

RNA Isolation, Northern Blotting and Southern Blotting of Genomic DNAs. Total cellular RNA was isolated by the guanidinium/phenol procedure and Northern blotting was performed as described (30–32). Ten pg of RNA were denatured with glyoxal/dimethyl sulfoxide (DMSO), electrophoresed on 1.0% agarose gels, transferred to nylon membranes and hybridized to a $^{32}$P-labeled mda-9 probe and then after stripping the membranes were hybridized to a $^{32}$P-labeled rat GAPDH probe (33) as described previously (30–32). Following hybridization, the filters were washed and exposed for autoradiography. RNA blots were quantitated by densitometric analysis using a Molecular Dynamics densitometer (Sunnyvale, CA) (34). To determine human tissue specific expression of mda-9 a Human RNA Master Blot™ (Clontech Laboratories, Inc., Palo Alto, Calif.), containing poly A RNA from 50 tissues immobilized as separate dots on a charged nylon membrane, was probed with a $^{32}$P-labeled mda-9 cDNA probe and following stripping the membrane was probed with a $^{32}$P-labeled human ubiquitin housekeeping cDNA probe as described by Clontech Laboratories, Inc. Following hybridization, the filters were washed and exposed for autoradiography.

Genomic DNAs for *Saccharomyces cerevisiae* (yeast), cat, dog, Rhesus monkey and normal human were obtained commercially (Promega Corp., Madison, Wis. and Clontech Laboratories Inc., Palo Alto, Calif.). Human DNA was also prepared from HeLa human cervical carcinoma cells. The DNAs were digested completely with HindIII restriction enzyme, electrophoresed, transferred to nylon membranes and hybridized to a $^{32}$P-labeled mda-9 gene probe (16,18, 32). After hybridization the nylon membranes were washed in 3×SSC, 0.1% SDS, 30 min; 1×SSC, 0.1% SDS, 30 min; and 0.1×SSC, 0.1% SDS, 20 min at 55° C.; and then exposed to autoradiography (18).

Reagents. Recombinant human IFN-β, with a serine substituted for a cysteine at position 17 of the molecule (35), was provided by Triton Bioscience (Alameda, Calif.). IFN-β was obtained as a lyophilized powder with a concentration of $4.5\times10^7$ U/ml. Recombinant human IFN-α (IFN-αA) was provided by Hoffmann-La Roche, Inc., N.J. Recombinant human IFN-γ was kindly provided by Dr. Sidney Pestka (UMDNJ-Robert Wood Johnson Medical School, N.J.). The interferon titer of IFN-αA and IFN-β was determined using a cytopathic effect inhibition assay with vesicular stomatitis virus (VSV) on a bovine kidney cell line (MDBK) or human fibroblast AG-1732 cells (36). The interferon titer of IFN-γ was determined using a cytopathic effect inhibition assay with VSV on the human WISH cell line (36). The concentrated stocks of interferons were diluted to $1\times10^6$ U/ml in DMEM-10, frozen at −80° C., thawed immediately prior to use, and diluted to the appropriate concentration in DMEM-10. Stock solutions were maintained at 4° C. MEZ was obtained from Sigma Scientific Co. (St. Louis, Mo.). Stock solutions were prepared in DMSO, aliquoted into small portions, and stored at −20° C. The final concentration of DMSO did not alter growth or induce markers of differentiation (elevated melanin synthesis) in the cell lines used in the present study.

EXPERIMENTAL RESULTS mda-9 Is Variably Expressed in H0-1 Cells Treated with IFN-β+MEZ. The subtraction hybridization strategy employed to identify genes involved in terminal cell differentiation has a high probability of detecting genes that display elevated expression in IFN-β+MEZ treated versus actively proliferating control H0-1 human melanoma cells (11). However, since cDNA libraries were constructed from pooled RNA samples obtained from H0-1 cells treated for various times with IFN-β+MEZ, i.e., 2, 4, 8, 12 and 24 h, it is equally possible that genes displaying biphasic patterns of gene expression can also be isolated from this TSS cDNA library. This is indeed the case as found with mda-9 which displays maximum enhanced expression 8 and 12 h after treatment with IFN-β+MEZ, whereas expression is lower than controls after 1 or 24 h treatment (FIG. 1). Exposure to IFN-β+MEZ for 2 or 4 h also elevates mda-9 expression, but to a lesser extent than after 8 or 12 h. On the basis of this study, if subtracted cDNA libraries had been produced solely from H0-1 cells treated for 24 h with IFN-β+MEZ the probability of isolating mda-9 cDNA clones would be significantly reduced. In this context, the temporally spaced subtracted (TSS) IFN-β+MEZ cDNA library should permit the cloning of additional genes that only display elevated expression in human melanoma cells during specific times within the first 24 h of treatment with IFN-β+MEZ.

mda-9 Is Down-Regulated in Terminally Differentiated Human Melanoma Cells. Treatment of human melanoma cells with IFN-β+MEZ (2000 U/ml+10 ng/ml) for 96 h results in growth suppression and terminal cell differentiation in the majority of treated cells (13,14,17). When grown in the single agent, growth suppression is less and the degree of inhibition depends on the specific melanoma analyzed (Table 1). Moreover, cultures treated with a single agent are not terminally differentiated (data not shown). The combination of agents either synergistically or additively reduces growth, depending on the melanoma cell line studied. Growth suppression induced by the combination of agents in specific melanomas is independent of the in vitro growth rate of these cells. For example, a >90% inhibition in growth is seen following 96 h treatment with IFN-β+MEZ in slow growing human melanomas, such as L0-1 and SKMEL-p53wt, as well as rapidly growing human melanomas, such as H0-1 and WM239. Maximum growth suppression, >95% in comparison with untreated control cultures, is apparent in human melanoma cells, H0-1, L0-1 and SKMEL-p53 wt, encoding a wild-type p53 protein (Table 1). Two human melanoma cells with a previously defined mutation in p53, MeWo and SKMEL-p53 mut, display <75% reduction in growth when treated with IFN-β+MEZ. In contrast, WM239, with an immunologically mut p53 protein, displays a different profile of sensitivity than the other melanoma cells. WM239 cells treated with IFN-β+MEZ are inhibited by ~91% when grown in the combination of agents (Table 1). Growth of the SV40-immortalized human melanocyte cell line, FM516-SV, in IFN-β+MEZ results in an ~70% reduction in growth without inducing terminal differentiation in the majority of treated cells (17) (Table 1 and data not shown).

Figure 2:
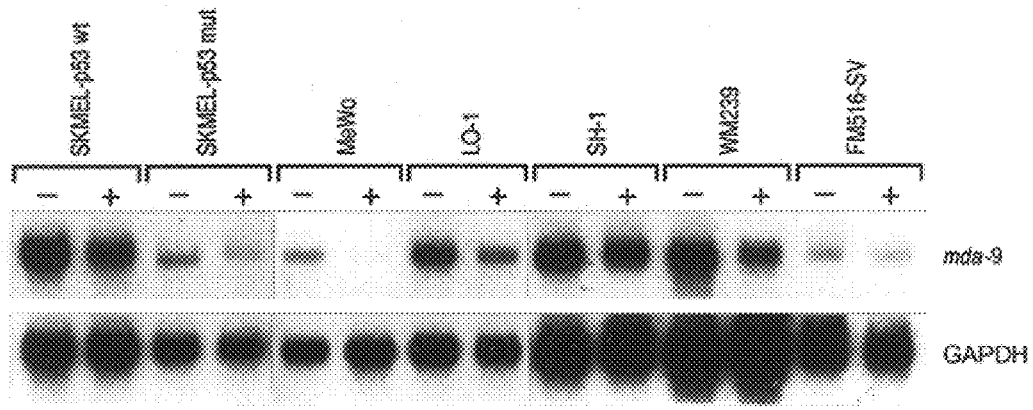
FIG. 2. Effects of IFN-β+MEZ on mda-9 expression in human melanoma cells and an SV40-immortalized human melanocyte cell line. The indicated cell line was grown in the presence or absence of IFN-β+MEZ (2000 U/ml+10 ng/ml) for 96 h and RNA was analyzed as described in FIG. 1.

To determine if induction of differentiation modifies mda-9 expression, RNAs were isolated from human melanoma and FM516-SV cells grown for 96 hr in the absence or presence of IFN-β+MEZ (2000 U/ml+10 ng/ml) (FIG. 2). In all of the cell lines, the combination of IFN-β+MEZ decreases the steady-state level of mda-9 RNA. Based on densitometer comparisons of mda-9 and GAPDH RNA levels, mda-9 RNA expression is reduced from ~1.5- to ~14-fold in treated cultures, with MeWo cells showing the greatest change and FM516-SV cells displaying the smallest change. A direct relationship between the level of reduction in mda-9 expression and the degree of growth suppression induced by IFN-β+MEZ is not apparent in the melanoma cell lines used in the present study.

TABLE 1

Effect of IFN-β and MEZ, alone and in combination, on the growth of human melanoma and melanocyte cell lines Experimental Conditions[a]

| Cell Line | Control | IFN-β | MEZ | IFN-β + MEZ |
| --- | --- | --- | --- | --- |
| H0-1 | 64.5 ± 5.3 | 14.0 ± 2.6 (22) | 16.8 ± 1.0 (26) | 0.7 ± 0.2 (1) |
| L0-1 | 17.0 ± 2.0 | 1.3 ± 0.3 (8) | 4.7 ± 0.4 (28) | 0.4 ± 0.1 (2) |
| MeWo | 33.6 ± 1.2 | 15.6 ± 1.9 (46) | 15.4 ± 1.9 (46) | 9.4 ± 1.1 (28) |
| SH-1 | 24.9 ± 1.6 | 14.3 ± 1.5 (57) | 14.1 ± 0.3 (57) | 8.0 ± 1.2 (32) |
| SKMEL-p53 mut | 36.1 ± 4.8 | 39.5 ± 7.5 (109) | 21.5 ± 4.3 (60) | 9.3 ± 0.6 (26) |
| SKMEL-p53 wt | 16.8 ± 0.8 | 9.1 ± 0.3 (54) | 3.6 ± 0.7 (21) | 0.7 ± 0.2 (4) |
| WM239 | 49.8 ± 1.8 | 9.5 ± 0.9 (19) | 19.7 ± 1.2 (40) | 4.4 ± 0.4 (9) |
| FM516-SV | 21.2 ± 1.7 | 7.8 ± 1.0 (37) | 12.7 ± 1.8 (60) | 6.2 ± 0.6 (29) |

[a]Cells were seeded at 5 × 10⁴ cells per 35-mm tissue culture plate and 24 h later the medium was changed with the indicated compounds, control = medium without additions, IFN-β = 2000 U/ml, MEZ = 10 ng/ml, and IFN-β + MEZ = 2000 U/ml + 10 ng/ml. Cell numbers were determined by Coulter Counter after 96-h growth. Results are the average of triplicate plates ± S.D. Bold values in brackets indicate percent of control growth.

Figure 3:
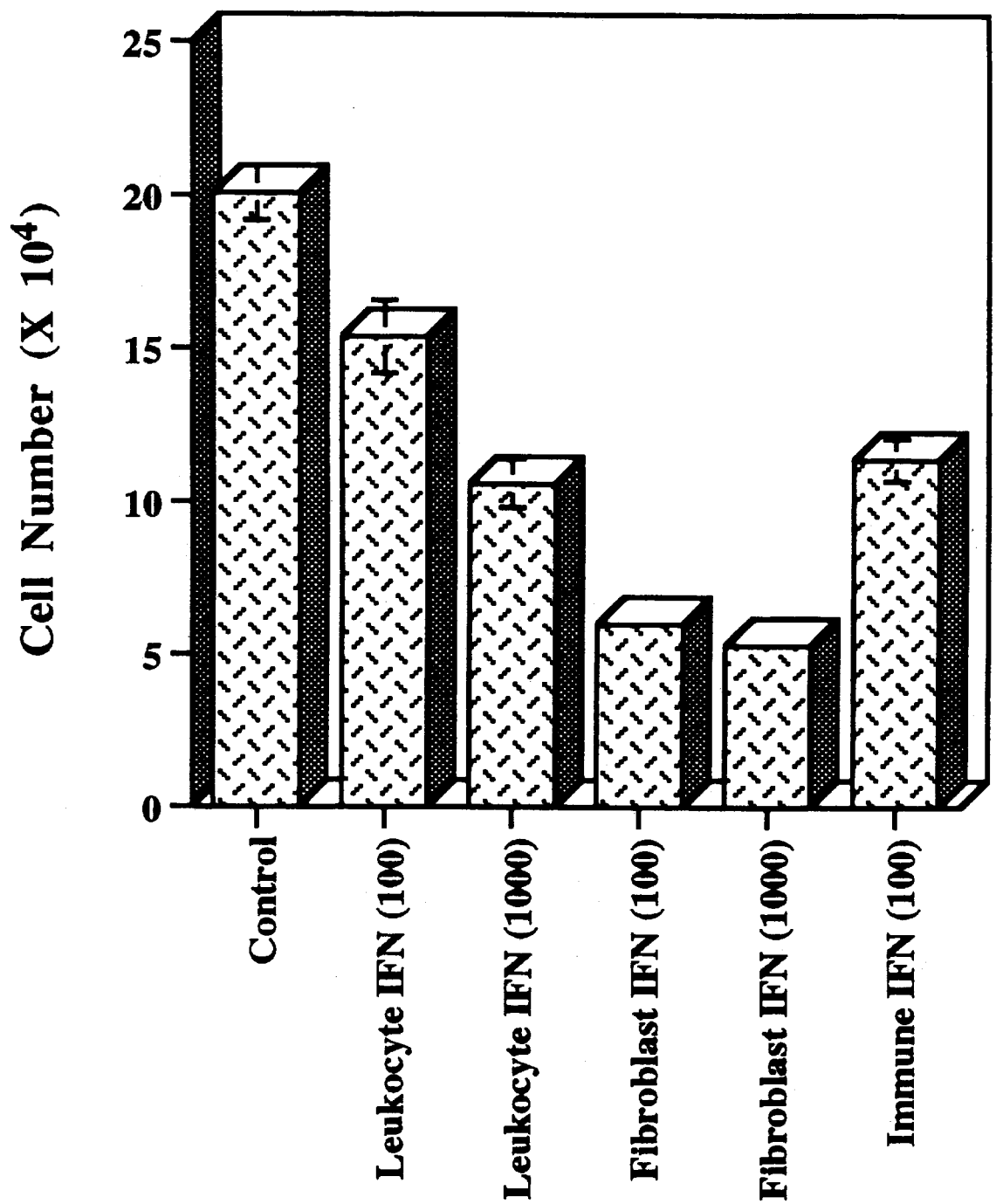
FIG. 3. Effect of interferons on growth of H0-1 cells. Cells were grown for 96 h in the absence or presence of IFN-α (100 and 1000 U/ml), IFN-β (100 and 1000 U/ml) or IFN-γ (100 U/ml) and cell numbers in triplicate plates were determined. Results are the average cell number±S.D. from the mean.
Figure 4:
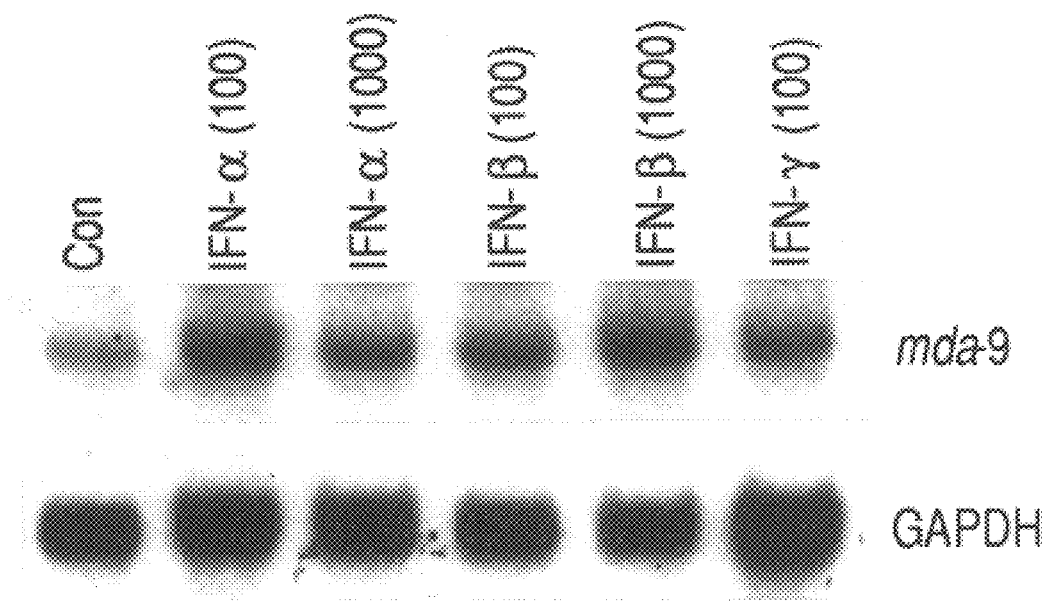
FIG. 4. Effect of interferons on mda-9 expression in H0-1 cells. H0-1 cells were grown for 96 h in the absence or presence of IFN-α (100 and 1000 U/ml), IFN-β (100 and 1000 U/ml) or IFN-γ (100 U/ml)and RNA was analyzed as described in FIG. 1.
Figure 5:
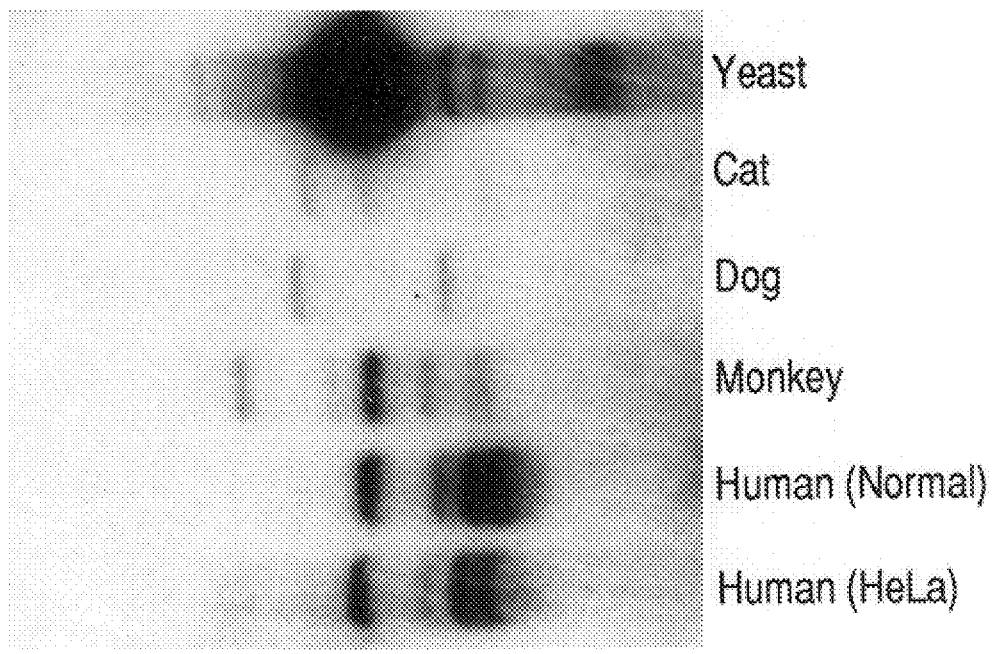
FIG. 5. Evolutionary conservation of the genomic mda-9 sequences. Genomic DNA (8 μg) isolated from different species, yeast (*Saccharomyces cerevisiae*), cat, dog, monkey (Rhesus) and human (normal and HeLa), were digested with HindIII. The digested DNAs were electrophoresed, transferred to nylon filters, hybridized with $^{32}$P-labeled mda-9 gene probe and exposed to autoradiography.
Figure 6:
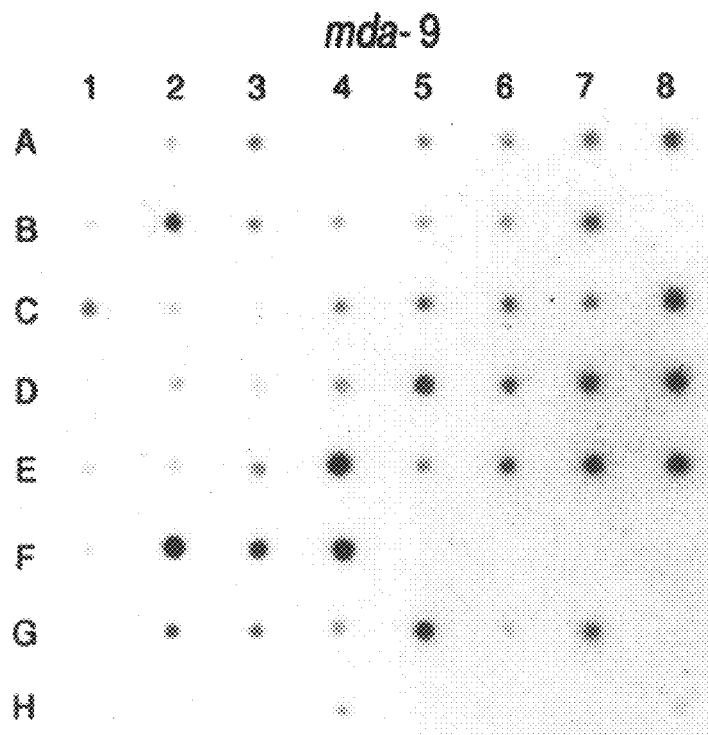
FIGS. 6A–6C. Expression of mda-9 in human tissues. A positively charged nylon membrane containing poly $A^+$ RNAs from the 50 tissues indicated was hybridized with an mda-9 probe and exposed to autoradiography. The nylon membrane was stripped, reprobed with a ubiquitin probe and exposed to autoradiography.
Figure 6B:
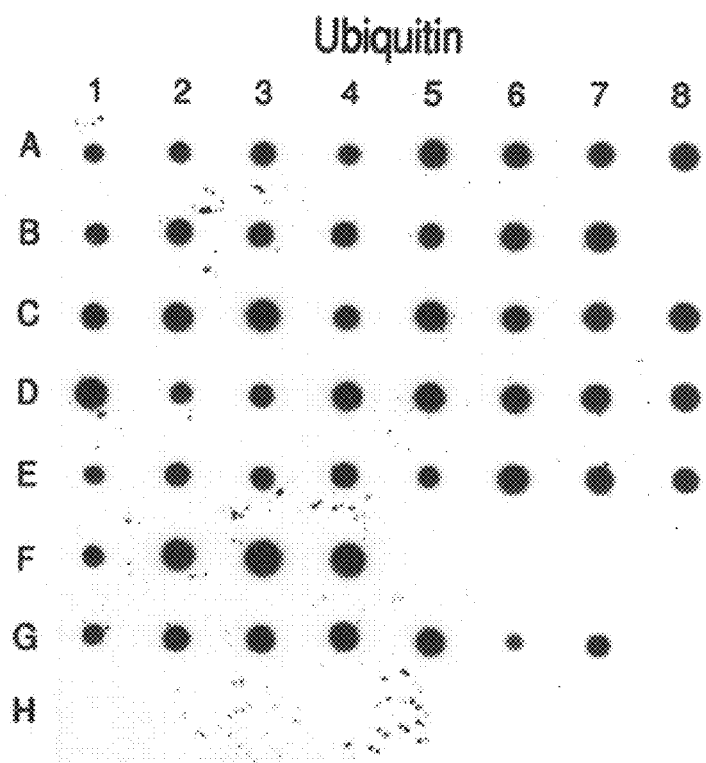

Treatment of H0-1 Cells with Interferon Induces Growth Suppression While Enhancing mda-9 Expression. Experiments were performed to determine if a relationship exists between growth suppression and reduced mda-9 expression. To test this connection, the effect of interferon and MEZ treatment on proliferation and mda-9 expression in human melanoma cells was determined. Growth of H0-1 cells in the presence of type I interferon, IFN-α or IFN-β, or type II interferon, IFN-γ, suppresses the growth of H0-1 cells (FIG. 3). IFN-β is the most effective interferon in inhibiting H0-1 growth, with an ~70% reduction after 4 d treatment with 100 U/ml. Under similar experimental conditions, 100 U/ml of IFN-γ reduces growth by ~43% and 100 U/ml of IFN-α reduces growth by only 23%. Unlike IFN-β+MEZ, which reduce mda-9 expression in H0-1 cells, all three interferons enhance mda-9 expression ~1.9- to ~4.0-fold based on equalization for GAPDH expression (FIG. 4). In contrast, mda-9 expression is unaffected in H0-1 cells grown for 4 days in 10 ng/ml of MEZ, even though growth is reduced by ~74% (Table 1 and data not shown). These results indicate that growth suppression in H0-1 cells can be dissociated from decreased mda-9 expression.

mda-9 Is an Evolutionary Conserved Gene. To determine if sequences homologous to human mda-9 are present in the genomes of other species Southern blotting analyses were performed using genomic DNAs from *Saccharomyces cerevisiae* (yeast), cat, dog, Rhesus monkey and human (normal and HeLa) (18) (FIG. 5). On the basis of intensity of hybridization in Southern blots, the greatest sequence homology occurs between monkey and human genomic DNAs. Hybridization with yeast DNA is also evident. The apparently high level of hybridization with the mda-9 probe is the result of an ~10-fold higher relative concentration of genomic yeast DNA added to this gel. Dog and cat genomic DNA display weaker hybridization after probing Southern blots with mda-9. These findings suggest that mda-9 is an evolutionary conserved gene.

mda-9 Is Expressed in Diverse Human Tissues. To determine the pattern of expression of the mda-9 gene a Human RNA Master Blot that contains poly $^+$A RNAs from 50 human tissues immobilized in separate dots on a nylon membrane was analyzed (FIG. 6A–6C). As a positive control for RNA expression the membranes were stripped and rehybridized with a ubiquitin cDNA probe (FIG. 6B). Both mda-9 and ubiquitin are expressed in all 50 human tissues. Comparing the intensity of hybridization between mda-9 and ubiquitin, elevated expression of mda-9 occurs in putamen, adult spleen and fetal spleen and reduced expression occurs in whole brain, amygdala, caudate nucleus, cerebellum, cerebral cortex, frontal lobe, hippocampus, medulla oblongata, occipital lobe, substantia nigra, temporal lobe, thalamus, subthalamic nucleus, spinal cord, heart, aorta, skeletal muscle, colon, bladder, uterus, prostate, stomach, testis, ovary, pancreas, pituitary gland, adrenal gland, thyroid gland, salivary gland, mammary gland, kidney, liver, small intestine, thymus, peripheral blood leukocytes, lymph node, bone marrow, appendix, lung, trachea and placenta. mda-9 and ubiquitin are also expressed in fetal brain, fetal heart, fetal kidney, fetal liver, fetal thymus and fetal lung. Hybridization with mda-9 also occurs with Escherichia coli DNA and with human genomic DNA (500 ng) (FIG. 6A). Longer exposures of the Human Master RNA Blot probed with ubiquitin indicates hybridization to human genomic DNA (both 100 and 500 ng), but no hybridization with *Escherichia coli* DNA (data not shown). No hybridization is observed with mda-9 or ubiquitin with yeast total RNA, yeast tRNA, *Escherichia coli* rRNA or poly r(A). The ability of mda-9 to hybridize to *Escherichia coli* suggests some homology to bacterial sequences. DNA data bank sequence searches indicate only minor homology within small regions of mda-9 and bacterial sequences. The ability of mda-9 to hybridize with human genomic DNA may indicate the presence of repetitive sequences or that this gene is highly abundant or a member of a multi-gene family. Analysis of multiple human tissue Northern blots also demonstrates fairly uniform mda-9 expression in multiple tissue types (data not shown).

EXPERIMENTAL DISCUSSION

The aberrant differentiation/modified gene expression model of cancer development is based on the hypothesis that specific forms of cancer may develop from defects in differentiation and gene expression that are inherently reversible (6–11,13,14). If these assumptions are correct, then it may be possible to induce the appropriate program of gene expression and a more normal differentiated phenotype in a cancer cell by treatment with the appropriate agent(s). This idea has been experimentally tested using cultured human melanoma cells (13,14,16). The combination of IFN-β+MEZ results in changes in the expression of a spectrum of genes, including cell cycle and growth regulating genes, and the induction of an irreversible loss in proliferative ability and terminal differentiation in malignant melanoma cells (13–18,34). By using the molecular approach of subtraction hybridization those changes in gene expression that correlate with and may control growth and differentiation in human cancer cells are being defined (16–20). This information offers potential for identifying potentially new cellular targets for the differentiation therapy of human cancer.

In the present study a novel mda-9 gene identified by subtraction hybridization that is down-regulated when human melanoma cells are induced to terminally differentiate is described. Decreased expression of mda-9 in H0-1 cells can be distinguished from growth suppression or induction of specific markers of differentiation, such as enhanced melanin synthesis and the formation of dendrite-like processes. For example, agents that suppress growth in H0-1 cells without inducing markers of differentiation, such as IFN-γ, elevate mda-9 expression, whereas MEZ, which can reversibly induce elevated melanin synthesis, growth suppression and dendrite-like processes in H0-1 cells, has no effect on mda-9 expression. These findings suggest that mda-9 may be a component of the terminal differentiation program in human melanoma cells. Southern blotting using genomic DNAs from different species indicates that mda-9 is an evolutionary conserved gene and analysis of multiple human tissue-derived mRNAs indicate that mda-9 is a widely expressed gene, with a small elevation in expression in the putamen (brain) and spleen (both adult and fetal). Nucleotide and amino acid sequence analysis of mda-9 indicate no significant homology to previously reported genes. However, two small stretches of homology, 22 of 69 (31%) and 11 of 45 (24%) identities and 36 of 69 (52%) and 22 of 29 (75%) positives, respectively, are apparent between mda-9 (aa 196 to 264 and aa 135 to 179) and the X11 gene product (aa 637 to 705 and 554 to 598) (37). The X11 gene encodes a protein that is expressed in the brain, primarily in the granular layer of the cerebellum, but is not detectable in several non-neuronal tissues and cell lines. The X11 gene encodes a protein of 708-aa with a putative transmembrane segment and may represent a candidate Friedreich ataxia gene (37). Since the homologies between mda-9 and X11 are so small, it is unlikely that these genes display functional similarities.

Further studies are required to determine the biological relevance of modified mda-9 expression in terminal differentiation in human melanoma cells. For example, overexpression of mda-9 in melanoma cells could be used to determine if preventing down-regulation of mda-9 can modify the differentiation process. Alternatively, inhibiting mda-9 expression by using antisense based technologies can also be used to evaluate the role of this gene in terminal differentiation in human melanoma cells. Additional studies are also required to determine if altered mda-9 expression is associated with the differentiation or growth processes in other cancer and normal cell types. Experiments to determine the spectrum of cytokine and differentiation-modulating agents that can affect mda-9 expression will also be informative.

The gene expression changes associated with and mediating terminal differentiation in human melanoma cells are complex, consisting of both increases and decreases in the abundance of specific RNA species (10–12,14–20,34). Unraveling the roles of those gene products that positively regulate differentiation phenotypes and that negatively regulate growth is essential in order to define terminal differentiation on a molecular level. Several models are possible for integrating these gene changes in the terminal differentiation process. A 'master-switch' gene may exist that can singularly induce the cascade of gene expression changes resulting in terminal differentiation, i.e., differentiation is a linear process initially controlled by a single genetic element. Treatment of cells with an agent(s) that induces terminal differentiation may result in the induction and suppression of parallel sets of genes that ultimately converge to induce terminal differentiation, i.e., differentiation involves multiple independent pathways resulting in the activation of common genes mediating terminal differentiation. Alternatively, several independent and overlapping pathways may control differentiation, i.e., differentiation involves feedback loops consisting of multiple genes that display either elevated or decreased expression and that control the expression of downstream genes and pathways critical for differentiation. Further studies should help clarify the molecular and biochemical processes that control the induction and maintenance of terminal differentiation in human melanoma cells and delineate the roles of specific mda genes in regulating these processes.

REFERENCES

1. Fisher, P. B., Enhancement of viral transformation and expression of the transformed phenotype by tumor promoters. In: T. J. Slaga, Ed., *Tumor Promotion and Cocarcinogenesis In Vitro, Mechanisms of Tumor Promotion*, pp. 57–123, CRC Press, Boca Raton, Fla., 1984.
2. Bishop, J. M., Molecular themes in oncogenesis. Cell, 64: 235–248, 1991.
3. Vogelstein, B., and Kinzler, K. W., The multistep nature of cancer. Trends Genet., 9: 138–141, 1991.
4. Knudson, A. G., Antioncogenes and human cancer. Proc. Natl. Acad. Sci. U.S.A., 90: 10914–10921,. 1993.
5. Hartwell, L. H., and Kastan, M. B., Cell cycle control and cancer. Science, 266: 1821–1828, 1994.
6. Waxman, S., Rossi, G. B., and Takaku, F., Eds., *The Status of Differentiation Therapy*, Vol. 1, Raven Press, New York, 1988.
7. Fisher, P. B., and Rowley, P. T., Regulation of growth, differentiation and antigen expression in human tumor cells by recombinant cytokines: applications for the differentiation therapy of cancer. In: Waxman, S., Rossi, G. B., and Takaku, F., Eds., *The Status of Differentiation Therapy of Cancer*, Vol. 2, pp. 201–213, Raven Press, New York, 1991.
8. Waxman, S., Rossi, G. B., and Takaku, F., Eds., *The Status of Differentiation Therapy*, Vol. 2, Raven Press, New York, 1991.
9. Waxman, S., Ed., *Differentiation Therapy, Challenges in Molecular Medicine*, Vol. 10, Ares-Serono Symposia Publications, Rome, Italy, 1995.
10. Chellappan, S. P., Giordano, A., and Fisher, P. B., The role of cyclin dependent kinases and their inhibitors in cellular differentiation and development. Current Topics in Microbiology and Immunology, Springer-Verlag, N.Y., in press, 1996.
11. Jiang, H., Lin, J., and Fisher, P. B., A molecular definition of terminal differentiation in human melanoma cells. Mol. Cell. Different., 2 (3): 221–239, 1994.
12. Jiang, H., Lin, J., Su, Z. -z., and Fisher, P. B., The melanoma differentiation associated gene-6 (mda-6), which encodes the cyclin-dependent kinase inhibitor p21, may function as a negative regulator of human melanoma growth and progression. Mol. Cell. Different., 4 (1) :67–89, 1996.
13. Fisher, P. B., Prignoli, D. R., Hermo, H., Jr., Weinstein, I. B., and Pestka, S., Effects of combined treatment with interferon and mezerein on melanogenesis and growth in human melanoma cells. J. Interferon Res., 5: 11–22, 1985.
14. Jiang, H., Su, Z. -z., Boyd, J., and Fisher, P. B., Gene expression changes associated with reversible growth suppression and the induction of terminal differentiation in human melanoma cells. Mol. Cell. Different., 1 (1): 41–66, 1993.
15. Jiang, H., Lin, J., Young, S. -m., Goldstein, N. I., Waxman, S., Davila, V., Chellappan, S. P., and Fisher, P. B., Cell cycle gene expression and E2F transcription factor complexes in human melanoma cells Induced to terminally differentiate. Oncogene, 11: 1179–1189, 1995.
16. Jiang, H., and Fisher, P. B., Use of a sensitive and efficient subtraction hybridization protocol for the identification of genes differentially regulated during the induction of differentiation in human melanoma cells. Mol. Cell. Different., 1 (3): 285–299, 1993.
17. Jiang, H., Lin, J., Su, Z. -z., Herlyn, M., Kerbel, R. S., Weissman, B. E., Welch, D. R., and Fisher, P. B., The melanoma differentiation-associated gene mda-6, which encodes the cyclin-dependent kinase inhibitor p21, is differentially expressed during growth, differentiation and progression in human melanoma cells. Oncogene, 10: 1855–1864, 1995.
18. Jiang, H., Lin, J. J., Su, Z. -z., Goldstein, N. I., and Fisher, P. B., Subtraction hybridization identifies a novel melanoma differentiation associated gene, mda-7, modulated during human melanoma differentiation, growth and progression. Oncogene, 11: 2477–2486, 1995.
19. Jiang, H., Lin, J. J., Tao, J., and Fisher, P. B., Suppression of human ribosomal protein L23A expression during cell growth inhibition by interferon-β. Oncogene, 14, in press, 1997.
20. Jiang, H., Lin, J., Su, Z. -z., Collart, F. R., Huberman, E., and Fisher, P. B., Induction of differentiation in human promyelocytic HL-60 leukemia cells activates p21, WAF1/CIP1, expression in the absence of p53. Oncogene, 9:3397–3406, 1994.
21. Giovanella, B. C., Stehlin, J. S., Santamaria, C., Yim, S. O., Morgan, A. C., Williams, L. J., Leibovitz, A., Fialkow, P. Y., and Mumford, D. M., Human neoplastic and normal cells in tissue culture. I. Cell lines derived from malignant melanomas and normal melanocytes. J. Natl. Cancer Inst., 56: 1131–1142, 1976.
22. Huberman, E., Heckman, C., and Langenbach, R., Stimulation of differentiated functions in human melanoma cells by tumor-promoting agents and dimethyl sulfoxide. Cancer Res., 39: 2618–2624, 1979.
23. Melber, K., Zhu, G., and Diamond, L., SV40-transformed human melanocyte sensitivity to growth inhibition by the phorbol ester 12-0-tetradecanoylphorbol-13-acetate. Cancer Res., 49: 3650–3655, 1989.
24. Herlyn, M., Human melanoma: development and progression. Cancer Metastasis Rev., 9: 101–112, 1990.
25. Frohman, M. A., Dush, M. K, and Martin, G. R., Rapid production of full-length cDNAs from rare transcripts: amplification using a single gene-specific oligonucleotide primer. Proc. Natl. Acad. Sci. U.S.A., 85: 8998–9002, 1988.

26. Loh, E. Y., Elliot, J. F., Cwirla, S. A., Lanier, L. L., and Davis, M. M., Polymerase chain reaction with single-sided specificity: analysis of T cell receptor delta chain. Science, 243: 217–220, 1989.
27. Ohara, O., Dorit, R. L., and Gilbert, W., Direct genomic sequencing of bacterial DNA: the pyruvate kinase 1 gene of Escherichia coli. Proc. Natl. Acad. Sci. U.S.A., 86: 6883–6887, 1989.
28. Sanger, F., Nicklen, S., and Coulson, A. R., DNA sequencing with chain-terminating inhibitors. Proc. Natl. Acad. Sci. U.S.A., 74: 5463–5467, 1977.
29. Su, Z. -z., Leon, J. A., Jiang, H., Austin, V. A., Zimmer, S. G., and Fisher, P. B., Wild-type adenovirus type 5 transforming genes function as trans-dominant suppressors of oncogenesis in mutant adenovirus type 5 transformed rat embryo fibroblast cells. Cancer Res., 53: 1929–1938, 1993.
30. Reddy, P. G., Graham, G. M., Datta, S., Guarini, L., Moulton, T. A., Jiang, H., Gottesman, M. M., Ferrone, S., and Fisher, P. B., Effect of recombinant fibroblast interferon and recombinant immune interferon on growth and the antigenic phenotype of multidrug-resistant human glioblastoma multiforme cell. J. Natl. Cancer Inst., 83: 1307–1315, 1991.
31. Su, Z. -z., Grunberger, D., and Fisher, P. B., Suppression of adenovirus type 5 E1A-mediated transformation and expression of the transformed phenotype by caffeic acid phenethyl ester (CAPE). Mol. Carcinog., 4: 231–242, 1991.
32. Jiang, H., Su, Z. -z., Datta, S., Guarini, L., Waxman, S., and Fisher, P. B., Fludarabine phosphate selectively inhibits growth and modifies the antigenic phenotype of human glioblastoma multiforme cells expressing a multidrug resistance phenotype. Intl. J. Oncol., 1: 227–239, 1992.
33. Fort, P., Marty, L., Piechaczyk, M., Sabrouty, S. E., Dani, C., Jeanteur, P., and Blanchard, J. M., Various rat adult tissues express only one major mRNA species from the glyceraldehyde-3-phosphate-dehydrogenase multigenic family. Nucleic Acids Res., 13: 1431–1442, 1985.
34. Jiang, H., Waxman, S., and Fisher, P. B., Regulation of c-fos, c-jun, and jun-B gene expression in human melanoma cells induced to terminally differentiate. Mol. Cell. Different., 1 (2): 197–214, 1993.
35. Mark, D. B., Lu, S. D., Creasey, A., Yamamoto, R., and Lin, L., Site-specific mutagenesis of the human fibroblast interferon gene. Proc. Natl. Acad. Sci. U.S.A., 81: 5662–5666, 1984.
36. Rehberg, G., Kelder, B., Hoal, E. G., and Pestka, S., Specific molecular activities of recombinant and hybrid leukocyte interferons. J. Biol. Chem., 257: 11497–11502, 1982.
37. Duclos, F., Boschert, U., Sirugo, G., Mandel, J. -L., Hen, R., and Koenig, M., Gene in the region of the Friedreich ataxia locus encodes a putative transmembrane protein expressed in the nervous system. Proc. Natl. Acad. Sci. U.S.A., 90: 109–113, 1993.

What is claimed is:

1. A method for identifying a compound that induces terminal differentiation in cancer cells comprising:
   a) incubating cancer cells with the compound; and
   b) measuring the biphasic expression of full-length melanoma differentiation associated gene mda-9 mRNA, encoding mda-9, a protein of 298 amino acids and a molecular weight of ~34 kDa, wherein the full-length mda-9 mRNA expression is elevated 8–12 hours after incubation followed by reduced full-length mda-9 RNA expression 24–96 hours after incubation, the reduced expression of full-length mda-9 mRNA indicating that the compound induces terminal differentiation in cancer cells.

2. A method of claim 1, wherein the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells and lymphoma cells.

3. A method for identifying a compound that alters the expression of full-length mda-9 mRNA in human melanoma cells comprising:
   a) incubating the human melanoma cells with the compound; and
   b) measuring the biphasic expression of full-length mda-9 DNA, encoding mda-9, a protein of 298 amino acids and a molecular weight of ~34 kDa, wherein the full-length mda-9 mRNA expression is elevated 8–12 hours after incubation followed by reduced full-length mda-9 mRNA expression 24–96 hours after incubation, indicating that the compound alters the expression of full-length mda-9 mRNA in human melanoma cells.

* * * * *